US011913878B2

(12) United States Patent
Wang et al.

(10) Patent No.: US 11,913,878 B2
(45) Date of Patent: Feb. 27, 2024

(54) METHOD OF DETERMINING PETROLEUM HYDROCARBON FRACTIONS IN A SAMPLE

(71) Applicant: CRC Care PTY LTD, Callaghan (AU)

(72) Inventors: Liang Wang, Callaghan (AU); Ying Cheng, Callaghan (AU); Ravi Naidu, Callaghan (AU)

(73) Assignee: CRC Care PTY LTD, Callaghan (AU)

( * ) Notice: Subject to any disclaimer, the term of this patent is extended or adjusted under 35 U.S.C. 154(b) by 0 days.

(21) Appl. No.: 17/637,002

(22) PCT Filed: Aug. 28, 2019

(86) PCT No.: PCT/AU2019/050912
§ 371 (c)(1),
(2) Date: Feb. 21, 2022

(87) PCT Pub. No.: WO2021/035273
PCT Pub. Date: Mar. 4, 2021

(65) Prior Publication Data
US 2022/0291122 A1 Sep. 15, 2022

(51) Int. Cl.
*G01N 21/35* (2014.01)
*G01N 33/24* (2006.01)

(52) U.S. Cl.
CPC ............ *G01N 21/35* (2013.01); *G01N 33/241* (2013.01); *G01N 2021/3595* (2013.01); *G01N 2201/123* (2013.01)

(58) Field of Classification Search
CPC .............. G01N 21/35; G01N 33/241; G01N 2021/3595; G01N 2201/123;
(Continued)

(56) References Cited

U.S. PATENT DOCUMENTS

| 5,161,409 | A | * | 11/1992 | Hughes | G01N 15/06 250/339.11 |
| 2012/0153160 | A1 | * | 6/2012 | Forrester | G01N 21/359 250/341.1 |
| 2018/0017540 | A1 | * | 1/2018 | Miao | G01N 21/3563 |

FOREIGN PATENT DOCUMENTS

| WO | WO-2014179684 A2 * | 11/2014 | ......... G01N 21/3563 |
| WO | WO 2016/187671 A1 | 12/2016 | |
| WO | WO2016187671 A1 | 12/2016 | |

OTHER PUBLICATIONS

Wang, et al.; "Novel Methodologies for Automatically and Simultaneously Determining BTEX Components Using FTIR Spectra," Talanta (2015), vol. 144, pp. 1104-1110.
European Patent Office; Supplementary European Search Report in EP19942995, dated Dec. 12, 2022, filed Jul. 6, 2022.
Australian Government; Examination Report in 2019463665, dated Jan. 5, 2023, filed Apr. 7, 2022.
(Continued)

*Primary Examiner* — Marcus H Taningco
(74) *Attorney, Agent, or Firm* — DUNLAP CODDING, P.C.

(57) ABSTRACT

The present invention relates to a method of determining petroleum hydrocarbon fractions (Cn) in a sample, the method including: inputting the sample into a chamber; emitting infrared light from an optical light source into the chamber with the sample; detecting at a detector a detected infrared light from the chamber; transforming the detected infrared light to a Fourier Transform Infrared (FTIR) spectrum of the sample at a processor, wherein the FTIR spectrum has wavenumbers between 4000 and 400 cm−1; processing the FTIR spectrum to identify sub-bands each having at least one doublet of sub-band peaks at respective wavenumbers in a second derivative curve of the FTIR spectrum using a second derivation algorithm implemented by the processor; comparing the at least one doublet of sub-band peaks to data indicative of known doublets of sub-band peaks at known wavenumbers for petroleum hydrocarbon fractions in the FTIR spectrum to classify the
(Continued)

petroleum hydrocarbon fractions in the sample; and determining a dominant petroleum hydrocarbon fraction of the petroleum hydrocarbon fractions in the sample based on a ratio of intensities of the sub-band peaks of the at least one doublet for each of the petroleum hydrocarbon fractions in the sample.

19 Claims, 10 Drawing Sheets

(58) Field of Classification Search
CPC ....... G01N 21/4738; G01N 2201/0221; G01N 2201/1237; G01N 33/2823
See application file for complete search history.

(56) References Cited

OTHER PUBLICATIONS

Wang, et al.; "Application of Infrared Spectrum for Rapid Classification of Dominant Petroleum Hydrocarbon Fractions for Contaminated Site Assessment," Spectrochimica Acta Part A: Molecular and Biomolecular Spectroscopy (2019), vol. 207, pp. 183-188.
International Search Report and Written Opinion (PCT/AU2019/050912), dated Aug. 28, 2019, 10 pages.
Wang, Liang, et al. "Application of infrared spectrum for rapid classification of dominant petroleum hydrocarbon fractions for contaminated sight assessment.", Spectrochimica Acta Part A: Molecular and Biomolecular Spectroscopy, vol. 207, available online Sep. 15, 2018, pp. 183-188.

* cited by examiner

METHOD OF DETERMINING PETROLEUM HYDROCARBON FRACTIONS IN A SAMPLE

TECHNICAL FIELD

The present invention relates to a method and apparatus for determining petroleum hydrocarbon fractions ($C_n$) in a sample. In particular, but not exclusively, the invention relates to determining alkanes in a soil sample.

BACKGROUND OF INVENTION

Petroleum is comprised of highly complex and varied mixtures of hydrocarbons. For example, crude oil can consist of hundreds of individual petroleum hydrocarbon (PHC) compounds that represent from 50 to 98% of the total weight of crude oil. The PHC fractions are defined by chemical structure, carbon number, and structure activity relationships. Equivalent carbon numbers ($C_n$) are used to describe the PHC fractions, which are based on a range of physical chemical properties and simple partitioning models. The chains under $C_7$, called naphtha's, which may be used as dry cleaning solvents, are very light and easily vaporised. The chains from $C_7$ to $C_{11}$ may be blended and used for petrol. The chains from $C_{12}$ to $C^{15}$ may be used for kerosene, and the chains from $C_{12}$ to $C_{30}$ may be used for diesel and other heavier fuel oils. Lubricating oils, such as engine and motor oil, have carbon chains above $C_{30}$. Hydrocarbons with higher carbon fractions, and longer the carbon chains, are considered as heavier fractions of PHCs. The heavier fractions of PHCs have high viscosity, density, and boiling points, and long residence times in soil.

When an oil spill or leakage occurs on land, the sequestration and diffusion of PHCs are subject to physical, chemical, and biological processes that further change their composition, toxicity, and distribution (partitioning) within soil, and are referred to as weathering processes. The highly volatile fractions of PHCs will evaporate into the gas phase of the porous medium and may be lost to the atmosphere, adsorbed on to soil solids, or dissolved into soil water or groundwater. Less volatile PHCs will diffuse as oil or non-aqueous liquid (NAPLs) forms, through the porous medium and may be trapped in pores or adsorbed by mineral and organic matter surfaces. Linear compounds up to $C_{30}$, for example, may dissipate within a month by volatilisation, decomposition and degradation. By contrast, compounds with up to $C_{37}$ need at least 200 days. Indeed, the tar fraction consisting of long and complex chains can persist for years in soil. Investigating the carbon fractions in a PHC contaminated site can provide valuable site assessment information for remediation.

To measure the fractions of $C_n$ of PHC contaminants in a sample, such as soil, the fractions are typically extracted by standardised soil extraction procedures before instrumental analysis. For volatile organic compounds, such as BTEX and petrol, methanol extraction may be used. For semi-volatile compounds, sonication and supercritical fluid extractions (SFE) are commonly employed.

High-performance liquid chromatography (HPLC) and gas chromatography (GC) are commonly used instrumental techniques for PHC analyses. GC with mass spectrometry (GC/MS) or flame ionisation detection (GC/FID) is generally used for individual PHC component determinations. However, these instrumental techniques suffer from disadvantages compared with in-situ analysis techniques, including associated laboratory costs, lengthy processing time, and degradation and cross contamination of the sample. In addition, these instrumental techniques provide only a 'snapshot' in time. Consequently, these techniques require frequent sampling intervals to provide representative temporal variations in PHC levels.

An alternative method for measuring PHCs in a sample is to use infrared (IR) analysis, whereby the PHCs are identified by their spectral bands. The analysis time and cost of IR methods are typically far less than the GC and HPLC based methodologies. For example, an existing method for determining petroleum hydrocarbon fractions ($C_n$) in a sample employs Fourier Transform Infrared Spectroscopy (FTIR) devices. These FTIR devices apply the Fourier Transform algorithm to transform time domain infrared data into frequency domain data to then determine the petroleum hydrocarbon fractions ($C_n$) in a sample. The existing FTIR devices measure an infrared absorption spectrum. Based on quantum theory, the vibration of an isolated molecule occurs at a single frequency when it absorbs or emits energy, which gives rise to the vibrational spectrum. Unfortunately, each vibrating molecule interacts with other surrounding molecules at a slightly different frequency. Thus, the observed FTIR spectrum line shape (band) typically consists of a series of more or less overlapping bands representing these absorbed or scattered individual molecules. Extracting information and identifying the components from an overlapping IR spectrum is a key issue for FTIR devices analysing a sample with an unknown mixture of PHCs.

Typically, these existing FTIR devices thus require the separation of heavily overlapped bands to be performed by an experienced user with some knowledge about the system being studied. Indeed, the most widespread existing method of band decomposition of the infrared spectrum waveforms for chemical bonds or species identification is visual inspection by a user of an FTIR device, which can be slow and unreliable.

The discussion of document, acts, materials, devices, articles and the like is included in this specification solely for the purpose of providing context for the present invention. Reference to any prior art in this specification is not, and should not be taken as, an acknowledgment or any form of suggestion that this prior art forms part of the common general knowledge in any country.

SUMMARY OF INVENTION

In one aspect of the present invention, there is provided a method of determining petroleum hydrocarbon fractions (CO in a sample, the method including: inputting the sample into a chamber; emitting infrared light from an optical light source into the chamber with the sample; detecting at a detector a detected infrared light from the chamber; transforming the detected infrared light to a Fourier Transform Infrared (FTIR) spectrum of the sample at a processor, wherein the FTIR spectrum has wavenumbers between 4000 and 400 $cm^{-1}$; processing the FTIR spectrum to identify sub-bands each having at least one doublet of sub-band peaks at respective wavenumbers in a second derivative curve of the FTIR spectrum using a second derivation algorithm implemented by the processor; comparing the at least one doublet of sub-band peaks to data indicative of known doublets of sub-band peaks at known wavenumbers for petroleum hydrocarbon fractions in the FTIR spectrum to classify the petroleum hydrocarbon fractions in the sample; and determining a dominant petroleum hydrocarbon fraction of the petroleum hydrocarbon fractions in the sample based on a ratio of intensities of the sub-band peaks of the at least one doublet for each of the petroleum hydrocarbon fractions in the sample.

In another aspect of the present invention, there is provided an apparatus for determining petroleum hydrocarbon fractions ($C_n$) in a sample, the apparatus including: a housing; a chamber disposed in the housing for inputting the sample therein; an optical light source disposed in the housing for emitting infrared light into the chamber with the sample; a detector for detecting a detected infrared light from the chamber; and a controller disposed in the housing having a processor and a memory in data communication with the processor, the controller being configured to: transform the detected infrared light to a Fourier Transform Infrared (FTIR) spectrum of the sample at a processor, wherein the FTIR spectrum has wavenumbers between 4000 and 400 $cm^{-1}$; process the FTIR spectrum to identify sub-bands each having at least one doublet of sub-band peaks at respective wavenumbers in a second derivative curve of the FTIR spectrum using a second derivation algorithm implemented by the processor; compare the at least one doublet of sub-band peaks to data indicative of known doublets of sub-band peaks at known wavenumbers for petroleum hydrocarbon fractions in the FTIR spectrum to classify the petroleum hydrocarbon fractions in the sample; and determine a dominant petroleum hydrocarbon fraction of the petroleum hydrocarbon fractions in the sample based on a ratio of intensities of the sub-band peaks of the at least one doublet for each of the petroleum hydrocarbon fractions in the sample.

Preferably, the at least one doublet includes a first doublet of sub-band peaks at wavenumbers between 3000 and 2800 $cm^{-1}$, a second doublet of sub-band peaks at wavenumbers between 1500 and 1400 $cm^{-1}$, and a third doublet of sub-band peaks at wavenumbers between 750 and 700 $cm^{-1}$.

Preferably still, the first doublet of sub-band peaks is at wavenumbers 2954 and 2827 $cm^{-1}$. Also, the second doublet of sub-band peaks is at wavenumbers between 1480 and 1450 $cm^{-1}$ and the third doublet of sub-band peaks is at wavenumbers between 750 and 730 $cm^{-1}$.

Infrared analyses in the region of 4000 to 400 $cm^{-1}$ are commonly used for chemical structure studies of petroleum hydrocarbon (PHC) fractions ($C_n$), including alkanes. Irrespective of the length of the carbon chains, all the PHC fractions have similar band patterns in infrared spectral modes. As mentioned, existing FTIR devices require that an experienced researcher with some knowledge about the system being studied attempts the separation of very overlapping bands in the FTIR spectrum.

In an example, a first doublet IR band between 3000 and 2800 $cm^{-1}$, and a second, smaller doublet IR band between 1500 and 1450 $cm^{-1}$ is present for all long chain alkanes. Further a third doublet of sub-band peaks at wavenumbers between 750 and 700 $cm^{-1}$ may also be present. These IR bands indicate the vibration of carbon hydrogen bindings. The signals in the mid-IR 'fingerprint' region (1500 to 700 $cm^{-1}$) are significantly weaker than higher wavelength regions. Additionally, they possess low signal to noise ratios with intensive bands overlapping. Further, in the example where the sample is soil, the second doublet and the third doublet of sub-band peaks are obscured in the FTIR spectrum by sub-bands for components of the soil.

Preferably, the infrared spectrum (4000 to 400 $cm^{-1}$) was applied to identify and classify the different alkanes based on carbon chain length ($C_n$) of the PHCs. It was found that there were two bands coherent to a doublet at location 2954 and 2872 $cm^{-1}$, respectively, which can be applied to classify the fraction of carbon chains. Further, from $C_{20}$ to $C_{37}$, by the increase of the $C_n$, the intensities of the two sub-bands were reduced. The intensity ratio of the coherent sub-bands can be applied to identify the dominant fraction of $C_n$. For example, four different petroleum products with different fractions of carbon chains in soil samples could be identified and classified, and the dominant fraction of carbon chain in the soil sample determined. In an embodiment, the apparatus is located near the sample. For example, the apparatus is a handheld FTIR, which makes it is possible to rapidly estimate the dominant fraction of $C_n$ in soil in field.

As mentioned, there may be another two doublets at the region from 1480 to 1450 $cm^{-1}$ and at the region at 750 and 730 $cm^{-1}$. In this embodiment, it was observed that the intensity of one coherent sub-band at each of these regions was increased following the increase on the $C_n$. The bands centre at 1462 and 730 $cm^{-1}$ were increased from $C_{20}$ to $C_{37}$.

In an embodiment, the method further includes performing baseline correction of the FTIR spectrum using a baseline correction algorithm implemented by the processor to: locate points on the FTIR spectrum representing wavenumbers with low absorbance values corresponding to valleys in the FTIR spectrum; recursively drawing a new baseline from both sides of the valleys to sides of the FTIR spectrum using straight lines; disregard ones of the points on the FTIR spectrum with absorbance values lower than the straight lines; and generate a baseline corrected FTIR spectrum by connecting remaining ones of the points on the FTIR spectrum. In this embodiment, the method further includes processing the baseline corrected FTIR spectrum to identify the sub-bands.

In an embodiment, the method further includes filtering the baseline corrected FTIR spectrum using a Gaussian filter algorithm implemented by the processor to remove ones of the sub-bands having sub-band valleys higher than a threshold value in the second derivative curve. In addition, the Gaussian filter algorithm may be a Gaussian low pass filter algorithm with a standard deviation of 1.5.

In an embodiment, the method further includes optimising identification of the sub-bands in the second derivative curve using an optimisation algorithm implemented by the processor to minimise a difference between a smoothed second derivative curve and the second derivative curve having the identified sub-bands. For example, the optimisation algorithm is a Monte Carlo algorithm.

BRIEF DESCRIPTION OF DRAWINGS

In order that the invention can be more clearly understood, examples of embodiments will now be described with reference to the accompanying drawings, in which.

DETAILED DESCRIPTION

Figure 1:
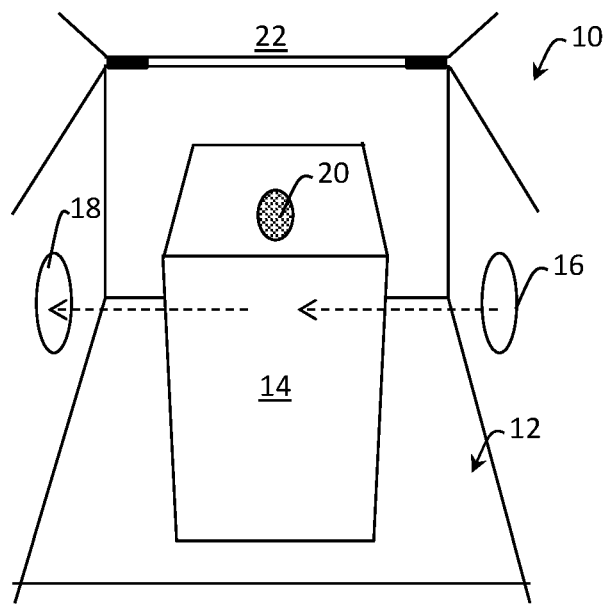
FIG. 1 shows a representation of an apparatus for determining petroleum hydrocarbon fractions ($C_n$) in a sample in a sample, according to an embodiment of the invention.

According to an embodiment of the present invention there is provided an apparatus 10 for determining petroleum hydrocarbon (PHC) fractions ($C_n$) in a sample, as shown in FIG. 1. The apparatus 10 includes a housing 12, a chamber 14 disposed in the housing 12 for inputting the sample therein at a sample inlet 20. The sample inlet 20 can also be configured to remove the sample from the chamber 20. The housing 12 includes an optical light source 16 disposed in the housing 12 for emitting infrared light into the chamber 14 with the sample and a detector 18 for detecting a detected infrared light from the chamber (not shown is a controller disposed in the housing having a processor and a memory in data communication with the processor).

The controller is configured to perform the following steps to determine petroleum hydrocarbon fractions ($C_n$) in a sample, the steps including: transforming the detected infrared light to a Fourier Transform Infrared (FTIR) spectrum of the sample at a processor, wherein the FTIR spectrum has wavenumbers between 4000 and 400 $cm^{-1}$; processing the FTIR spectrum to identify sub-bands each having at least one doublet of sub-band peaks at respective wavenumbers in a second derivative curve of the FTIR spectrum using a second derivation algorithm implemented by the processor; comparing the at least one doublet of sub-band peaks to data indicative of known doublets of sub-band peaks at known wavenumbers for petroleum hydrocarbon fractions in the FTIR spectrum to classify the petroleum hydrocarbon fractions in the sample; and determining a dominant petroleum hydrocarbon fraction of the petroleum hydrocarbon fractions in the sample based on a ratio of intensities of the sub-band peaks of the at least one doublet for each of the petroleum hydrocarbon fractions in the sample.

As mentioned, the hydrocarbon fractions ($C_n$) are preferably alkanes and the sample could be soil. The apparatus 10 is preferably a handheld FTIR device, and inspects the infrared spectrum wavelength between 4000 and 400 $cm^{-1}$ using FTIR. As demonstrated in FIG. 3, which shows the output of apparatus 10 in the region of 4000 and 400 $cm^{-1}$, and in the regions where doublets are shown. That is, in the region of a first doublet of sub-band peaks at wavenumbers between 3000 and 2800 $cm^{-1}$, a region of a second doublet of sub-band peaks at wavenumbers between 1500 and 1400 $cm^{-1}$, and a region of a third doublet of sub-band peaks at wavenumbers between 750 and 700 $cm^{-1}$.

The apparatus 10 was used, in the following examples, to demonstrate a rapid PHC fraction determination method for in-situ PHC assessment of a sample.

Figure 2:
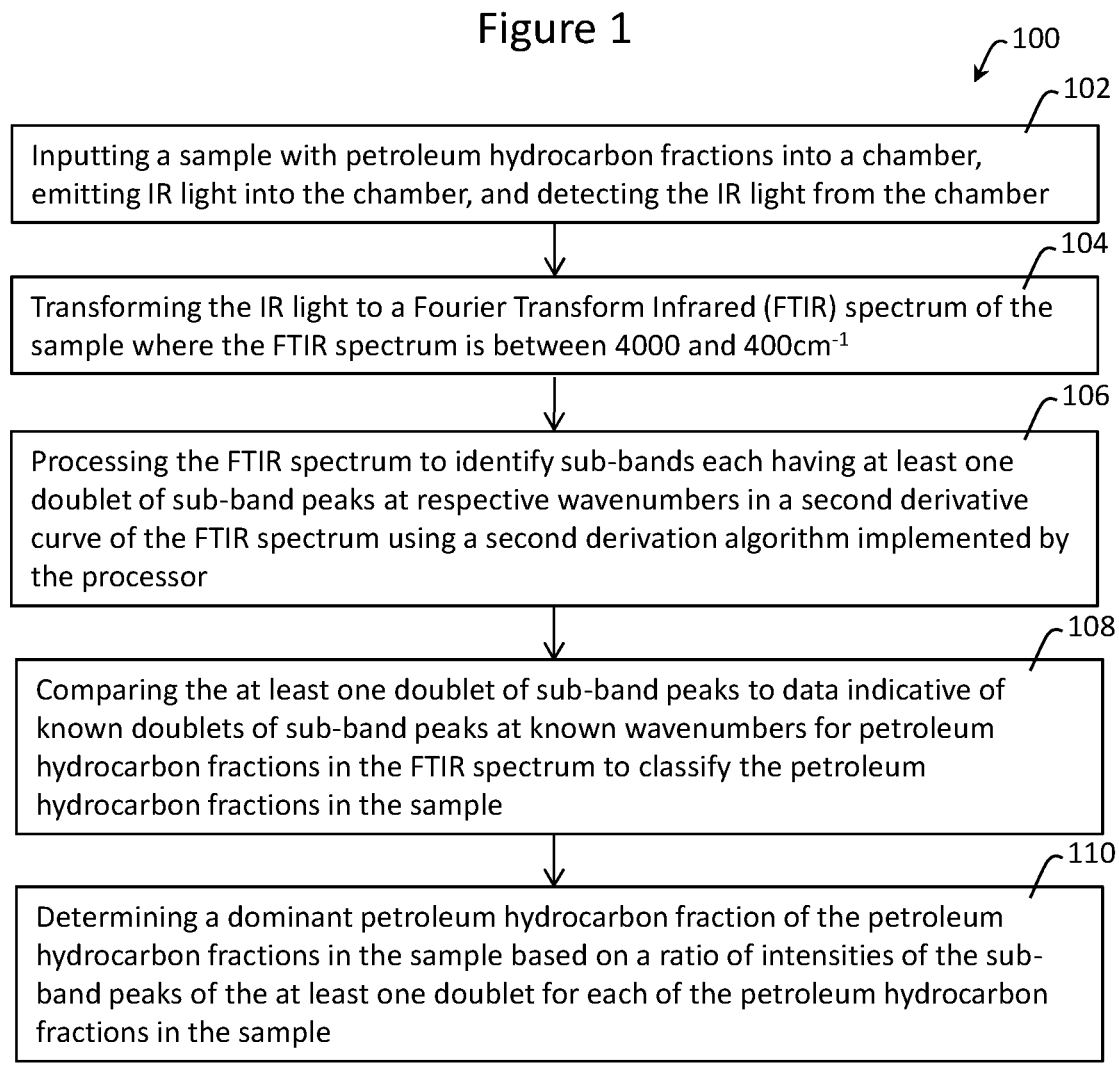
FIG. 2 shows a block diagram of a method of determining petroleum hydrocarbon fractions ($C_n$) in a sample, according to an embodiment of the invention.
Figure 3A:
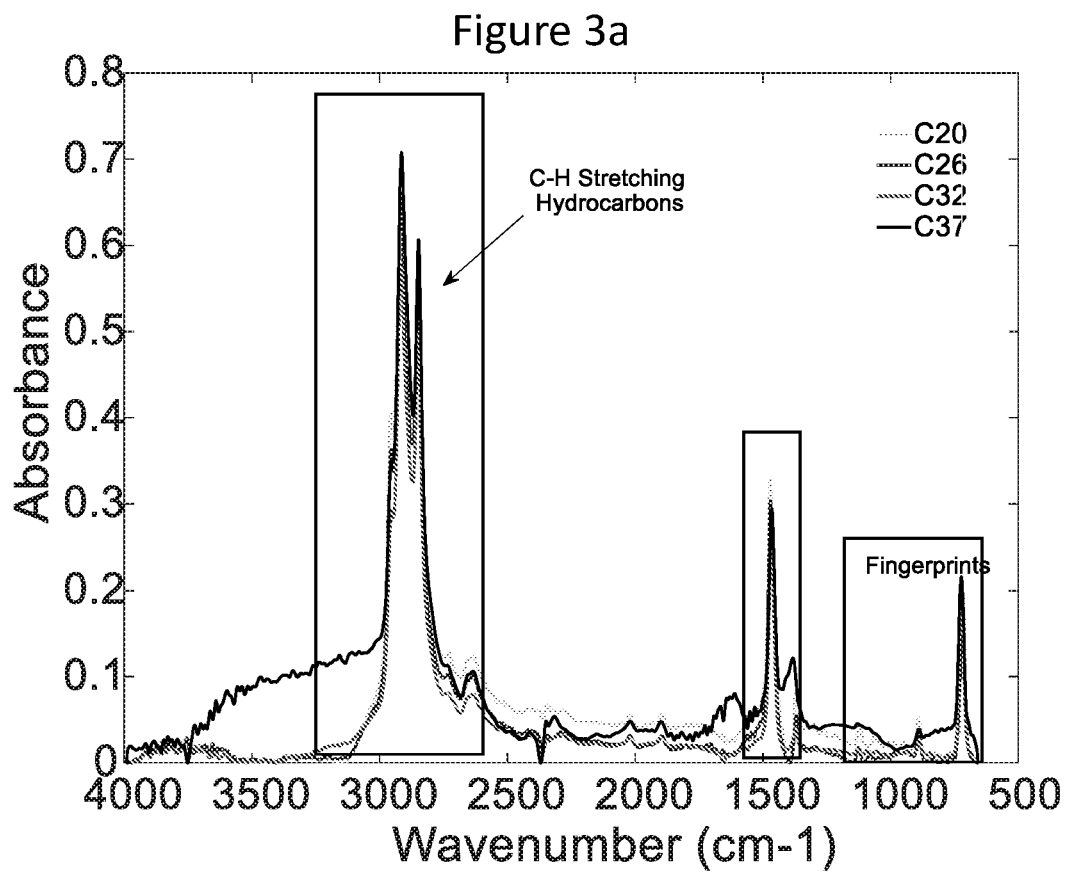
FIGS. 3a-3d shows the FTIR spectrum for alkanes in a sample after baseline correction, obtained according to an embodiment of the invention.
Figure 3B:
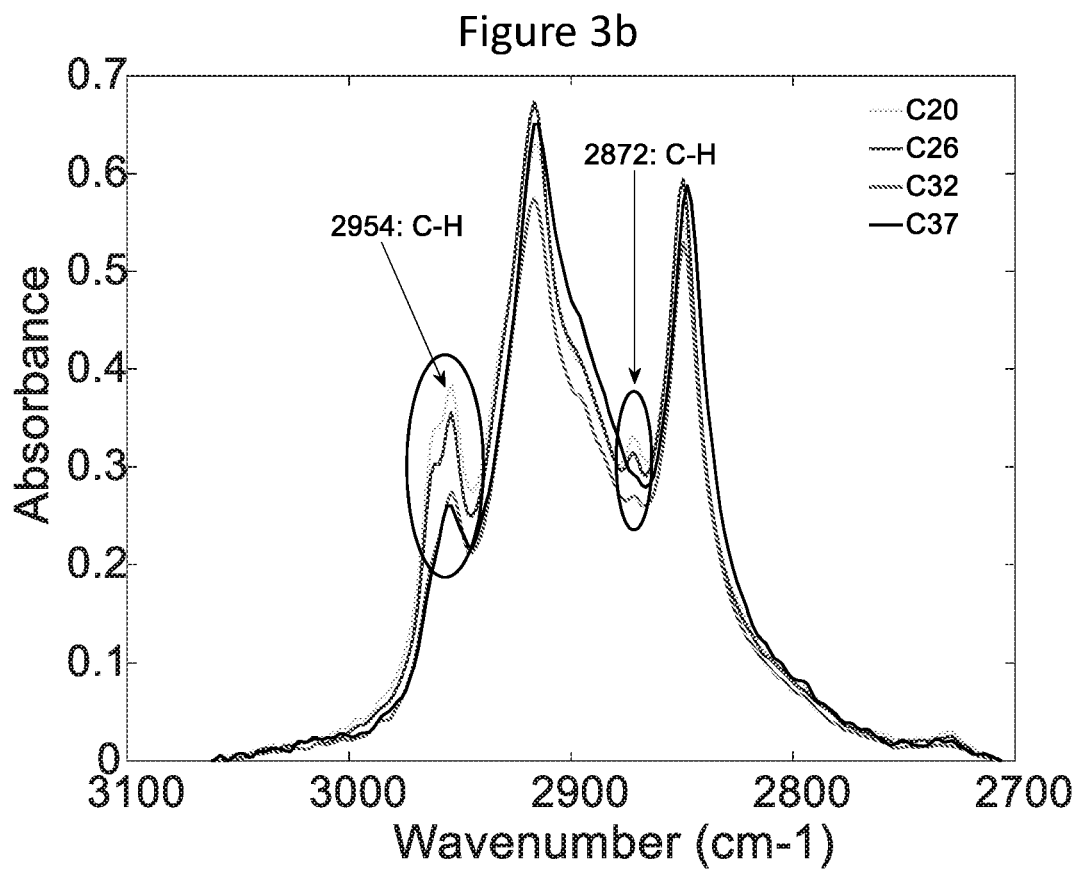
Figure 3C:
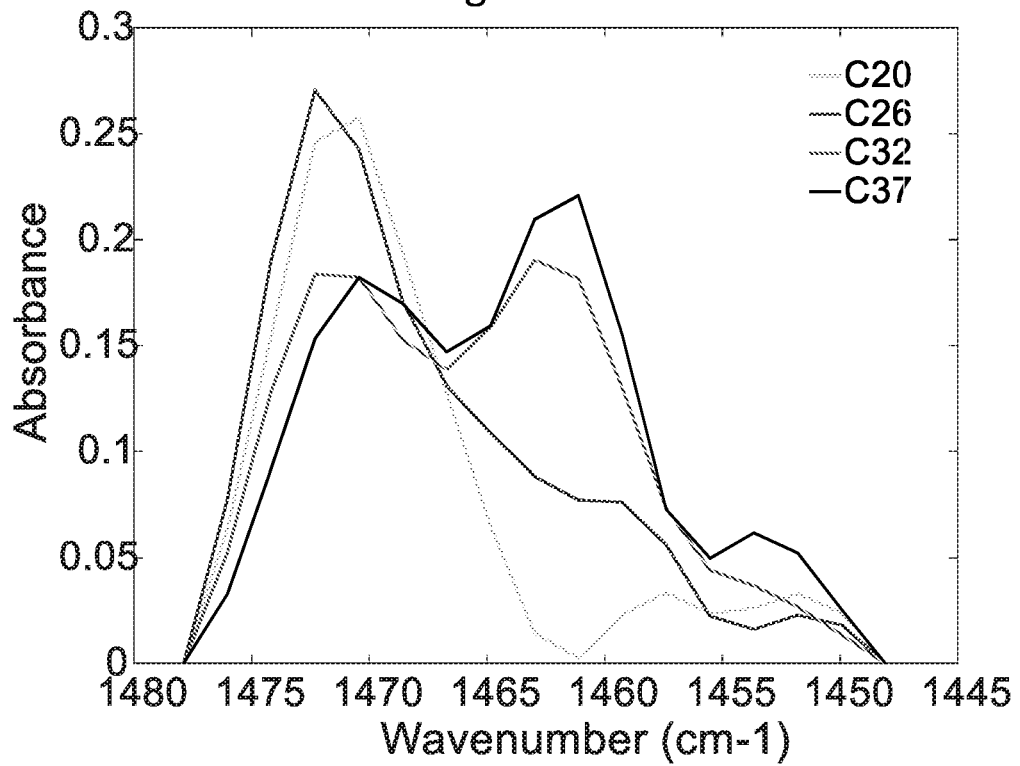
Figure 3D:
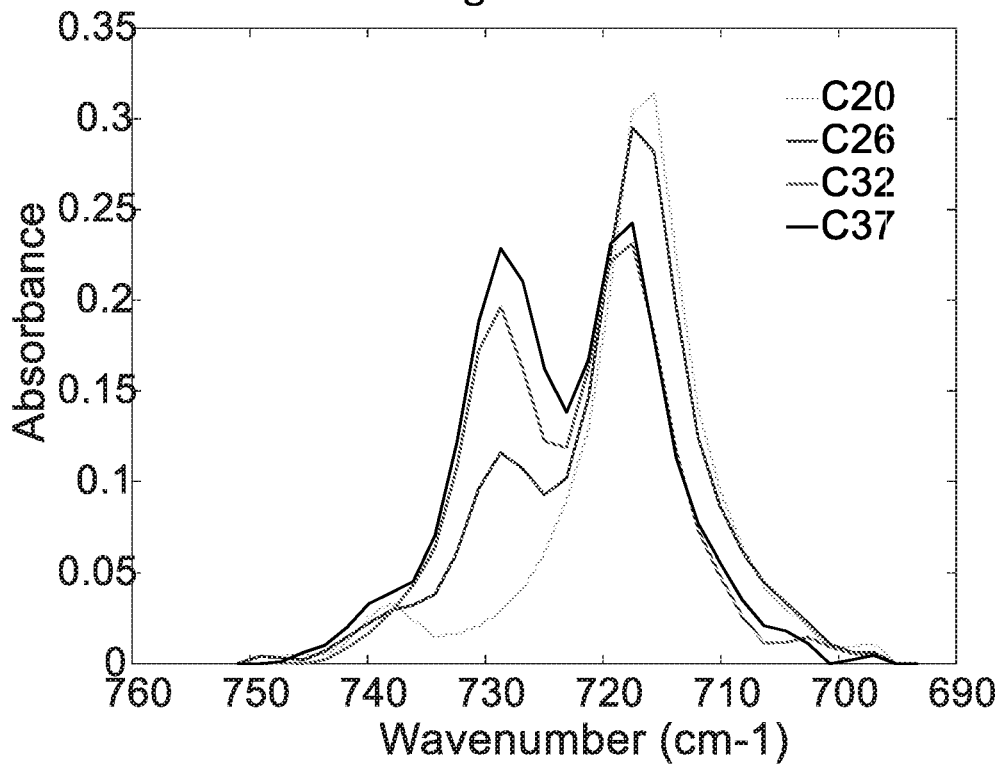
Figure 4A:
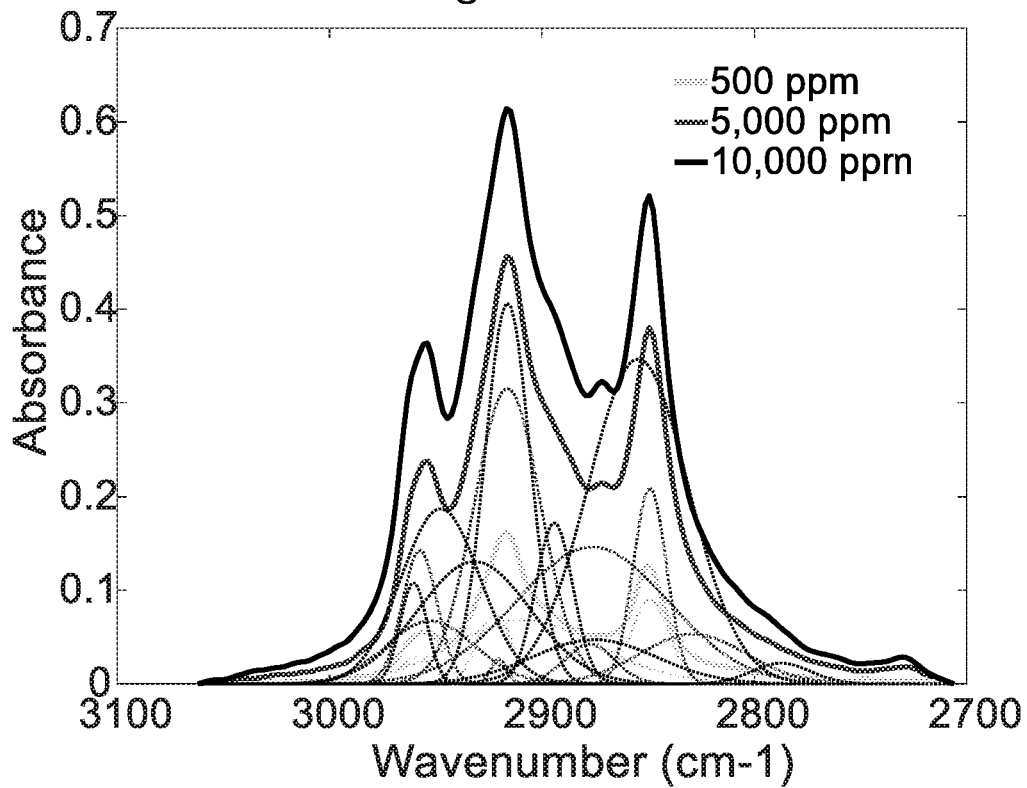
FIGS. 4a-4d shows the FTIR spectrum for selected alkanes, obtained according to an embodiment of the invention.
Figure 4B:
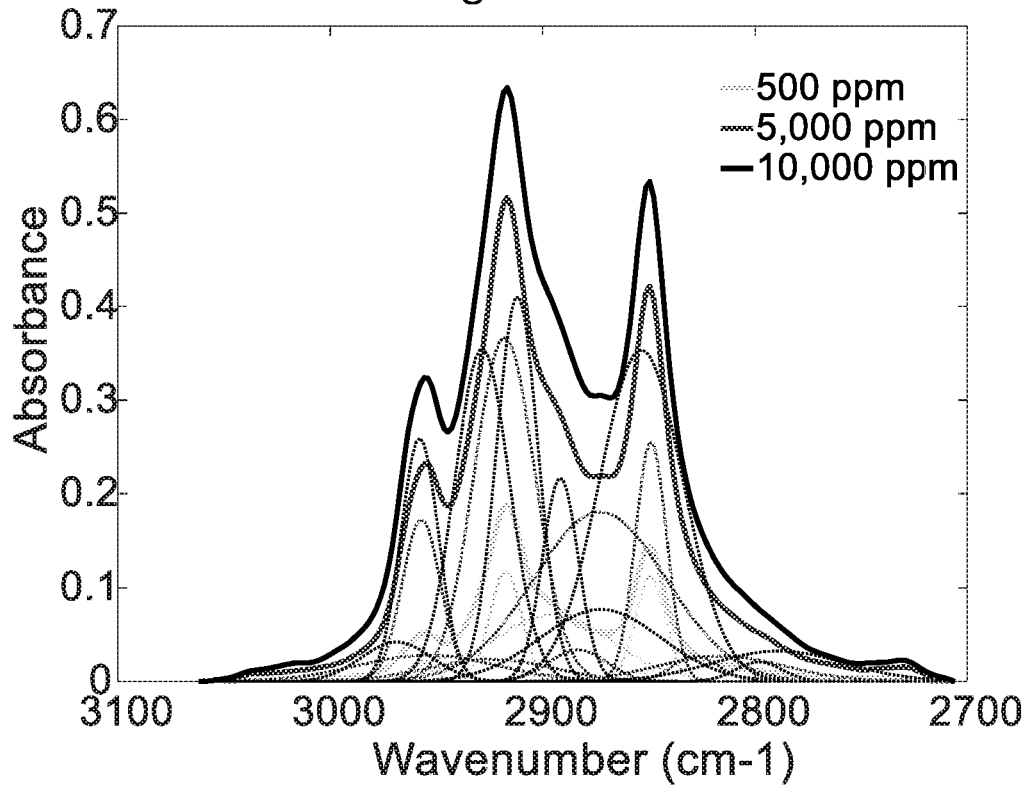
Figure 4C:
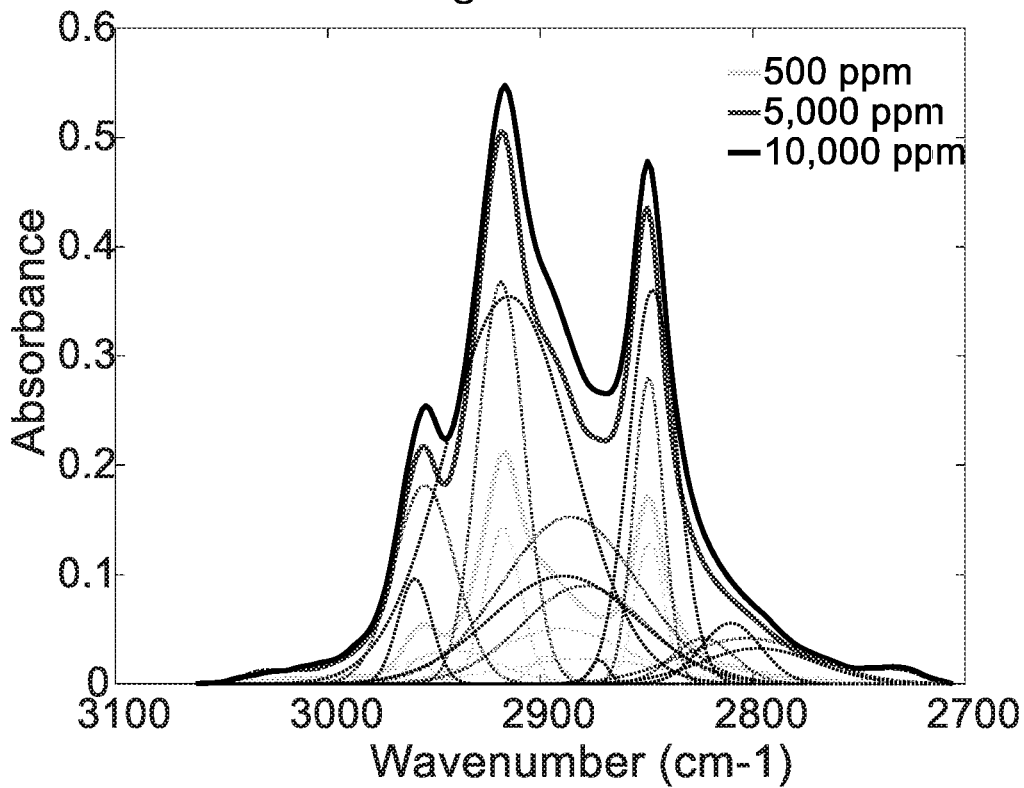
Figure 4D:
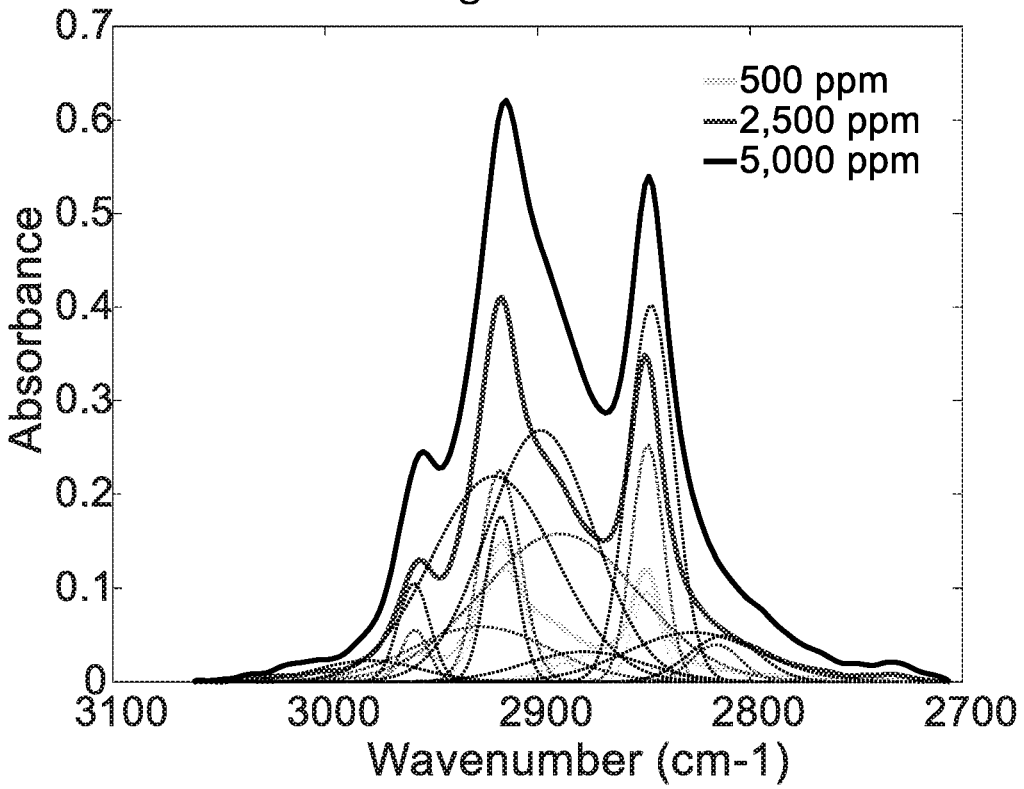

These examples further illustrate aspects of the method 100 of FIG. 2 and the apparatus 10 of FIG. 1.

In one example, pure chemicals of long chain alkanes: icosane ($C_{20}$), hexacosane ($C_{26}$), octacosane ($C_{28}$), dotriacontane ($C_{32}$) and heptatriacontane ($C_{37}$) were obtained. The pure alkane chemicals were added into hexane (95%) to create 20 mL of 10 g/L standard solutions for $C_{20}$ to $C_{32}$, and 5 g/L for $C_{37}$, respectively. It was observed that the alkanes with higher carbon chain numbers have lower a dissolution rate in hexane. 5 g/L $C_{37}$ solutions needed to be prepared with the assistance of ultrasonic vibrations. The individual alkanes were spiked into potassium bromide (KBr) for characteristic sub-band identification.

All the samples were measured in triplicate using a handheld FTIR, in the form of apparatus 10, with an 8 $cm^{-1}$ resolution, 32 sample scans, 64 background scans were co-added in the infrared 4000 to 600 $cm^{-1}$ region, at a scanning velocity of 2.5 kHz, and 255 beam energy. All measurements for the spiked soil samples were made in diffuse reflectance infrared spectroscopy (DRIFTS) mode, sample non-destructively. It should be mentioned that there are several levels of spectral resolution: from 8 to 2 $cm^{-1}$. The lower the number present, the higher resolutions, and the detection limits and spectral features for a given compound can be improved through higher resolutions which need high-resolution interferometers.

However, the relative cost to incorporate such a system for field monitoring would be exorbitant. Further, it would take a considerable amount of time for a scan and obtain point data for computational analysis. The sensitivity level chosen for this experiment is appropriate for reduced downtime and rapid screening for field related applications. With setting the resolution at 8 $cm^{-1}$, one measurement can be completed within thirty seconds with 32 scans.

Baseline Correction

In this example, a baseline correction algorithm, using computational recursion, was developed and applied to automate baseline correction for MIR (4000 to 400 $cm^{-1}$) spectra. The algorithm developed will run through all the spectral details and locate the lowest valley; then the baseline can be drawn by connecting the valleys to each side of the spectrum using straight lines. If any part of the spectrum is intersected by the straight lines after baseline correction, the spectrum will create negative absorbance values. In this case, the algorithm will be recursively run for the spectral regions where the intersecting straight lines connected. This simple and rapid baseline correction algorithm can be applied to any IR spectral region, without any intervention. Furthermore, since all the PHCs have similar spectral features, the adopted baseline correction algorithm can give unified baseline corrected IR data for all of the PHCs of interest.

Band Decomposition

An automatic band decomposition algorithm was applied in this example. The sub-bands were established using a second derivation curve (SDC). The band number can be controlled by eliminating the number of SDC valleys. The dominant bands from the original spectrum were presented as the lower valleys in the SDC. The small valleys, representing secondary bands, could be eliminated using a Gaussian low pass filter, with a standard deviation 1.5. The spectrum band can be properly decomposed using Gaussian curves, which the amplitude, width, and location were optimized using Monte Carlo algorithm (MCA), which is a heuristic algorithm based on randomness and statistics to get an optimisation result.

Thus, in the example, the infrared spectral data is first processed by automatically baseline correcting the IR spectra data and band decomposing the IR spectra without visual inspection. Quantitative analysis for each alkane was investigated using the decomposed sub-bands. Orthogonal experimental design (OED) was applied to generate the alkane mixtures with designed heterogeneous concentrations.

Results

The measurements for alkane classification in the example was conducted using four different alkanes, $C_{20}$, $C_{26}$, $C_{32}$ and $C_{37}$ with the concentration of 5000 ppm for each alkane, respectively. To prepare these standards, the pure alkane chemicals were diluted with potassium bromide (KBr). The four alkanes' spectra after background subtraction and baseline correction are shown in FIG. 3.a. According to the similarity of the IR bands in the entire region indicates the alkanes have identical molecular structures. The doublet observed between 3000 and 2800 cm$^{-1}$, which is the evidence of carbon hydrogen bonding for long-chain alkanes due to \\C\\H stretching vibrations. From the FIG. 3.b, it is found there were two bands coherent to the doublet at location 2954 and 2872 cm$^{-1}$, respectively.

From $C_{20}$ to $C_{37}$, by the increase of the $C_n$, the intensities of the two bands were reduced as demonstrated. This phenomenon matched similar results obtained from the Raman spectrum data of $C_8$ and $C_{20}$. In the Raman spectrum data, both the spectra of $C_8$ and $C_{20}$ contained all the similar bands, including the bands at location 2954 and 2872 cm$^{-1}$. It is observed that the band intensities of the $C_{20}$ were less than $C_8$ at these two locations. On the opposite, there were another two doublets existed in the region from 1480 to 1450 cm$^{-1}$ and the region at 750 to 730 cm$^{-1}$. It was observed that the intensity of one coherent band at each of these regions was increased following the increase on the $C_n$. As shown in FIGS. 3.c and d, the band centre at 1462 and 730 was increased from $C_{20}$ to $C_{37}$. As mentioned, the band near 730 cm$^{-1}$ can be seen only in long chain alkanes. The phenomena of the coherent bands in the three regions can be applied for $C_n$ classification.

For the quantification studies, three different concentration levels of each selected alkane were mixed with KBr, to generate the calibration standards of 500, 5000 and 10,000 ppm for $C_{20}$, $C_{26}$, $C_{32}$ and 500, 1000, 2500 and 5000 ppm for alkane $C_{37}$. All the calibration spectra of each selected alkane, including the baseline corrected and band decomposed spectra data, are demonstrated in FIG. 4. It is noted that the increasing concentration did significantly affect the absorbance magnitudes. Accordingly, based on the measurements, it was difficult to identify the characteristic bands when the alkanes present were less than 500 ppm for each alkane. In an ideal scenario when only a single alkane presented, the calibration for each alkane can be applied using the bands at this IR region after baseline correction. However, this ideal scenario does not fit into the petroleum products. For example, crude oil can consist of hundreds of individual petroleum hydrocarbon compounds. For the mixtures, the calibration should vary according to the characteristic bands of the sub-bands, after the decomposition, as shown in FIG. 4 for each alkane.

Figure 5:
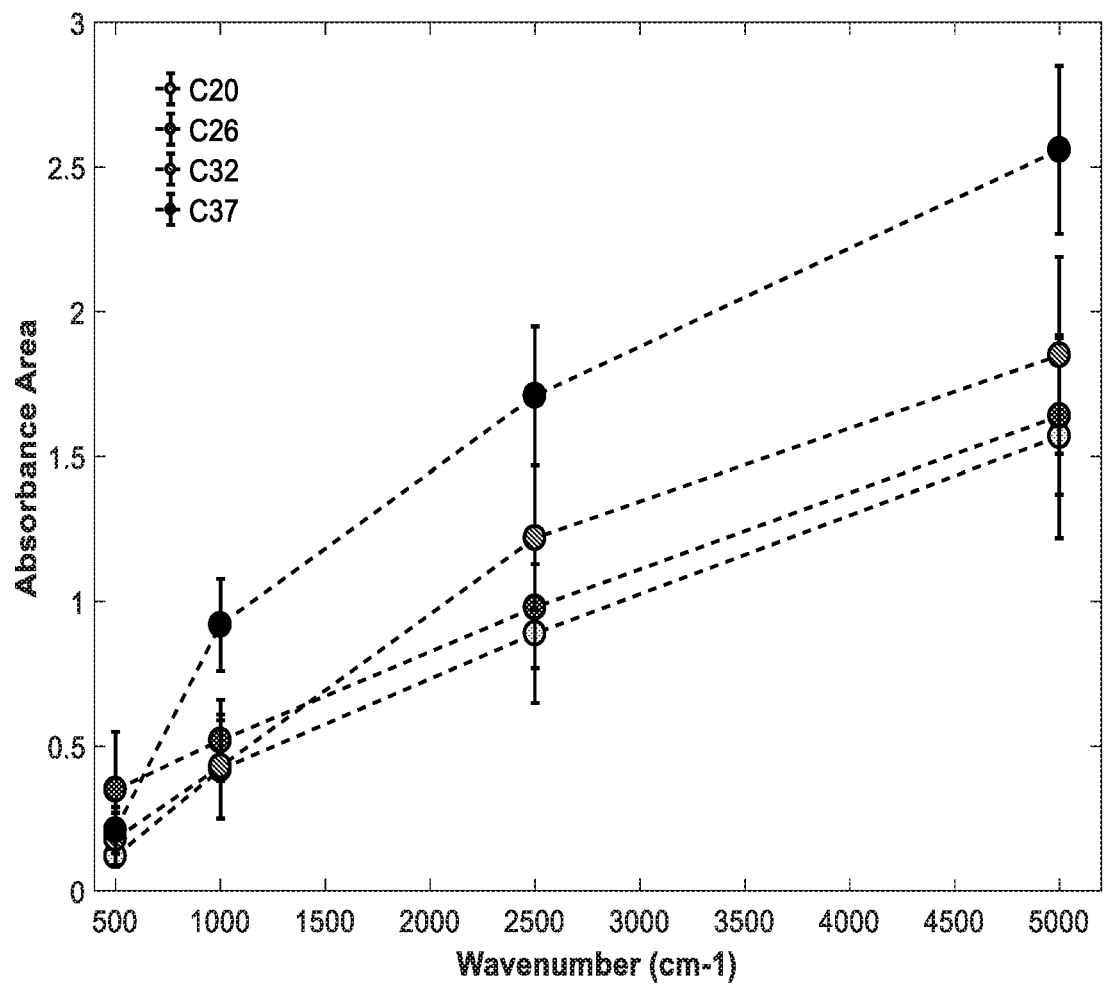
FIG. 5 shows the absorbance area value related to concentrations of each of the selected alkanes of FIGS. 4a-4d.
Figure 6A:
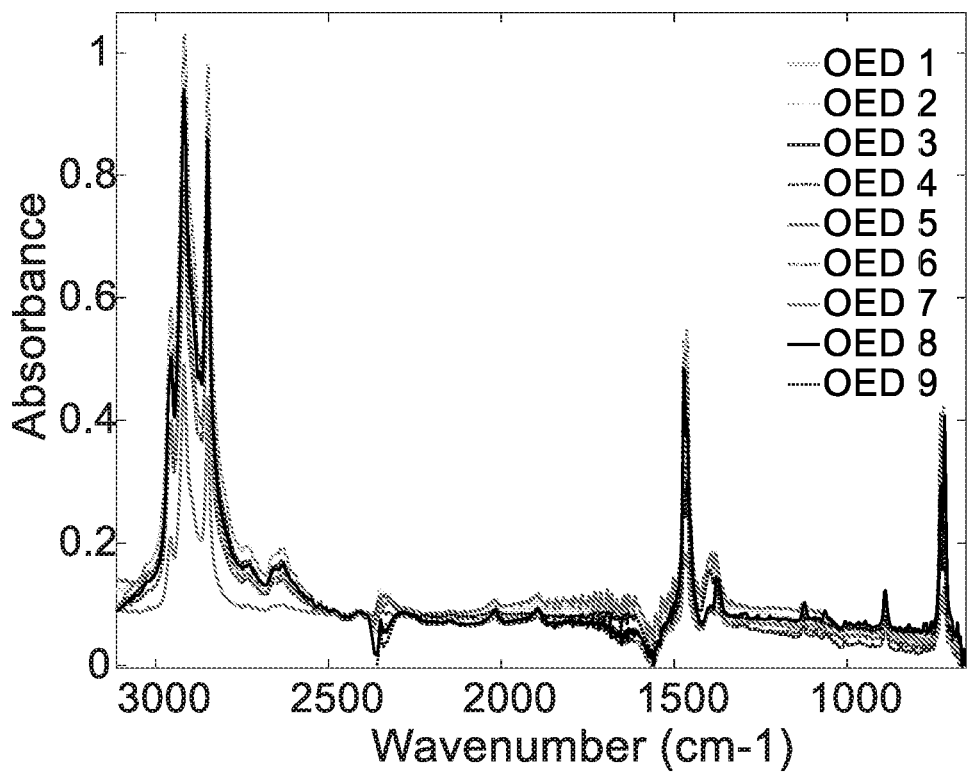
FIGS. 6a-6d shows the FTIR spectrum for a number of samples obtained according to an embodiment of the invention.
Figure 6B:
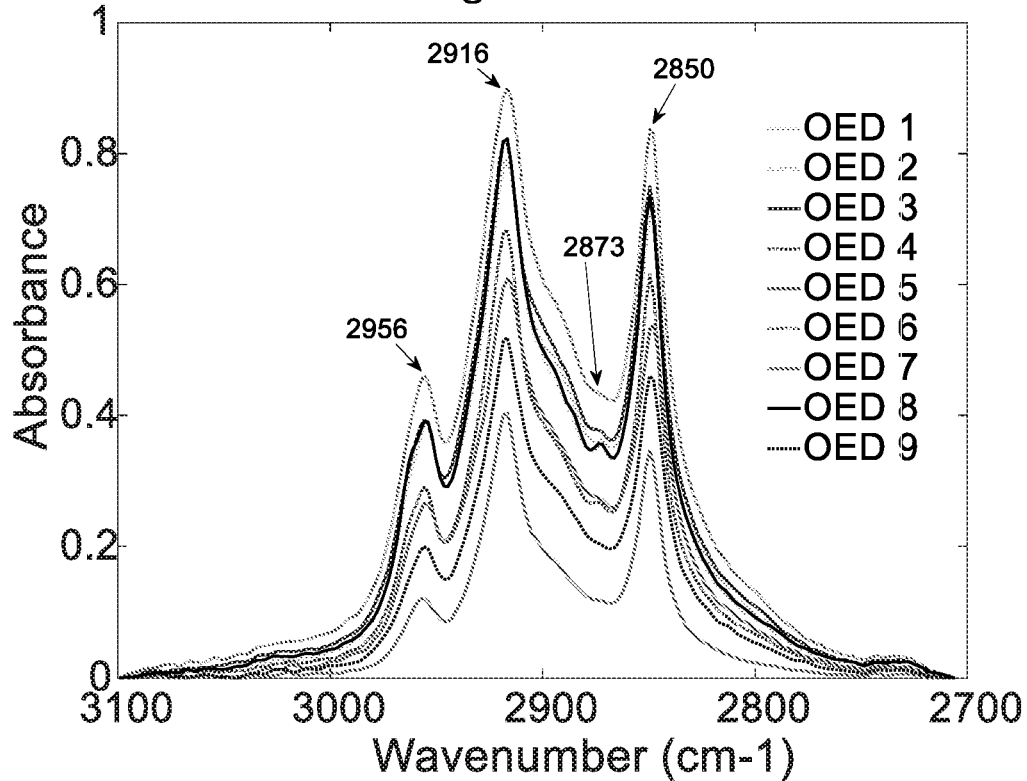
Figure 6C:
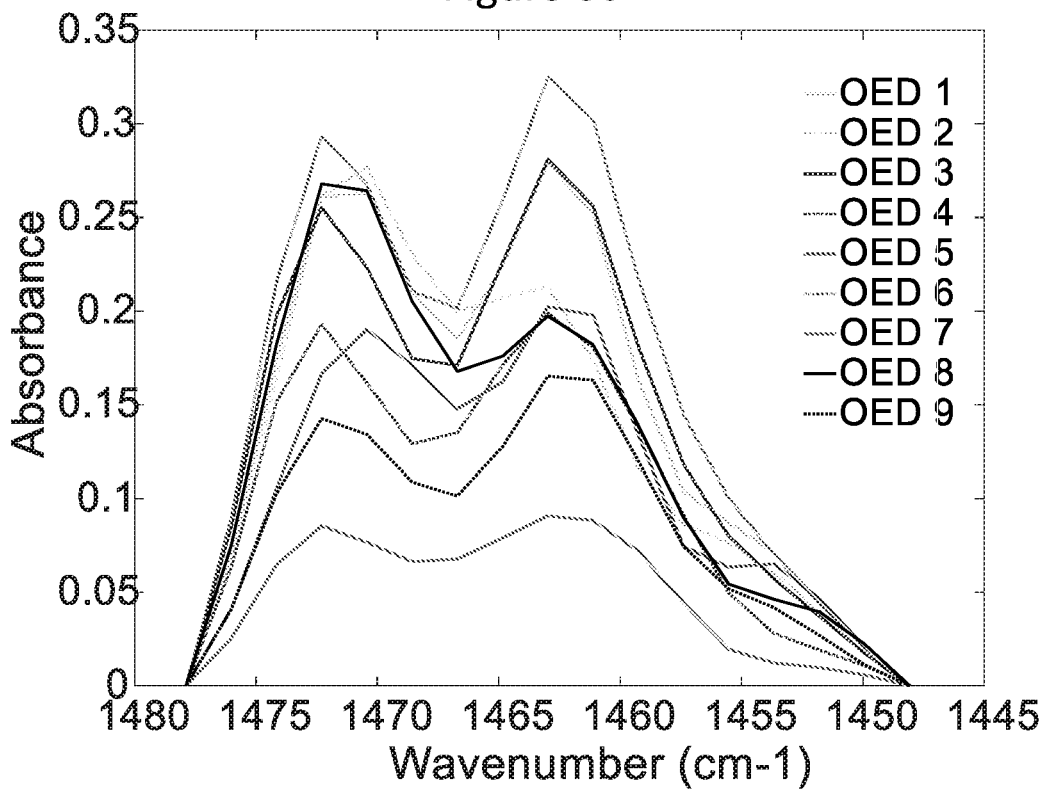
Figure 6D:
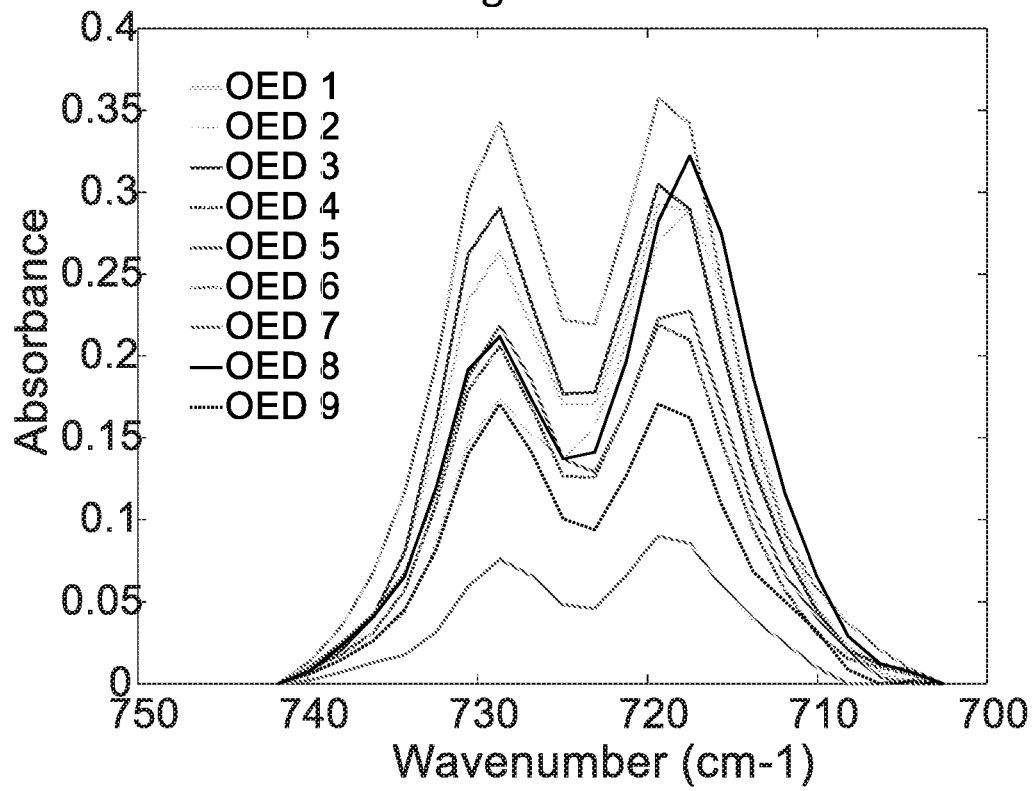

The calibration results of the four alkanes are illustrated in FIG. 5. Comparatively, all alkanes provided reasonable predictions when linking the absorbance area values to the spiked concentrations. FIG. 5 provides evidence that the concentrations were able to be predicted using the calibration curves generated with the single alkane standards.

In order to study the mixture scenario, orthogonal experimental design (OED) was applied to generate the alkane mixtures with designed heterogeneous concentrations. In an example, an orthogonal design table (ODT) was generated and contained nine synthetic mixtures of the selected alkanes, with three concentration levels mentioned before.

The mixtures were also prepared using an artificial soil containing 80% of quartz, 5% of humic acid and 15% of kaolinite. The details are listed in Table 1 and the spectral data for these nine mixtures are shown in FIG. 6. From FIG. 6.b, it is observed the minor band at 2873 cm$^{-1}$ which indicates the amount of $C_{20}$. For example, the band exists in the spectrum of OED 8 rather than OED 9, demonstrated with black continuous line and dash line, respectively. After band decomposition, the length carbon chains, $EC_n$ can be indicated with the ratio of band 2850 cm$^{-1}$ versus band 2956 cm$^{-1}$. Additionally, $EC_n$ can also be indicated by the ratio of the other two doublets at the regions 1489 to 1450 cm$^{-1}$ (FIG. 6.c) and region 750 to 700 cm$^{-1}$ (FIG. 6.d).

For example, the mixture OED 2 and 8, the proportion of shorter carbon chain ($C_{20}$ and $C_{26}$) were higher than the longer carbon chain ($C_{32}$ and $C_{37}$). It is observed the bands of 1470, and 715 cm$^{-1}$ were suppressed of 1460 and 730 cm$^{-1}$, respectively, as shown in FIG. 6.c and FIG. 6.d. These suppress phenomena are not shown in other spectral data from more homogeneous mixtures. The total concentration of the alkane mixture can be determined using absorbance area of a region below 3000 to 2800 cm$^{-1}$, as the EPA method 8440. In a mixture scenario, it is difficult to identify the specified $C_n$ from $C_{20}$ to $C_{37}$. Fortunately, the proportion of the shorter carbon chain ($C_{20}$ and $C_{26}$) and the longer carbon chain ($C_{32}$ and $C_{37}$) can be identified using the ratios as mentioned above.

To further validate the determination concept, 100 mg of four different petroleum products, were spiked separately into 1 g of the artificial soil. The details of the products are listed in Table 2.

Figure 7:
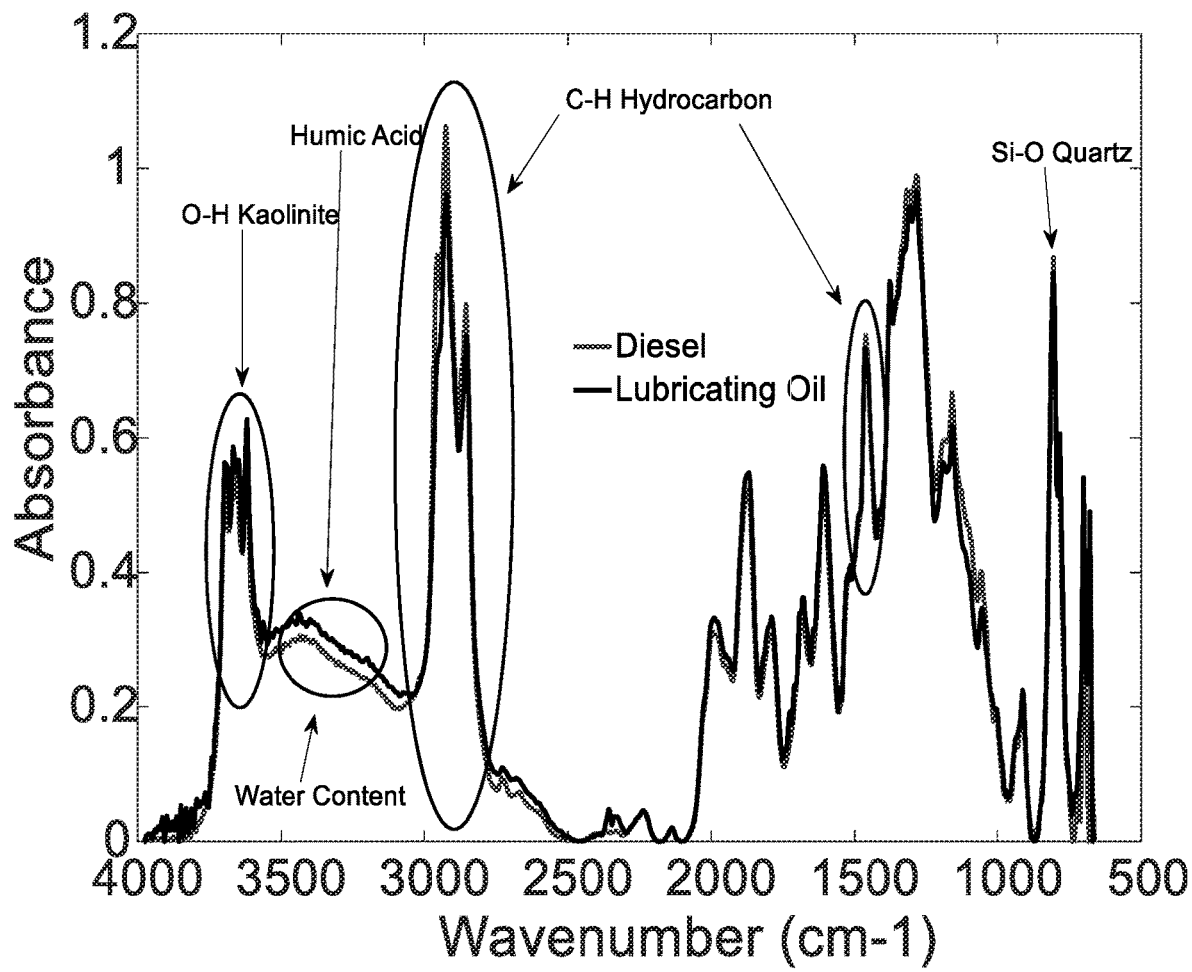
FIG. 7 shows the baseline corrected FTIR spectra data for the samples of FIGS. 6a-6d.

The products include petrol, kerosene, diesel, motor/lubricating oils, and grease wax. The density of each product was measured by weighing samples in 50 mL volume containers. From Table 2, as expected, the densities increased with the carbon chain numbers. All samples were prepared fresh daily, and measurements were carried out at room temperature (22° C.) in triplicate, and the average values are presented. As mentioned the artificial soil containing 80% of quartz, 5% of humic acid and 15% of kaolinite. It is observed the characteristic band at 804.5 cm$^{-1}$, indicating the Si\\O bending vibrations for quartz identification. Kaolinite can be identified with the strong O\\H stretching vibration presenting as the doublets at 3690 to 3620 cm$^{-1}$. Humic acid can be identified as the small bands like noise covered around 3500 cm$^{-1}$ and water content band central at around 3400 cm$^{-1}$. According to the spectrum in FIG. 7, the signal in below 2000 cm$^{-1}$ was dominated by quartz, and two of the hydrocarbon identical band regions at 740 to 710 cm$^{-1}$ and 1480 to 1450 cm$^{-1}$ were submerged in the dominated bands. Therefore, to avoid the interference from soil chemical components, the bands at 3000 to 2800 cm$^{-1}$ can be applied to the alkane studies.

Figure 8:
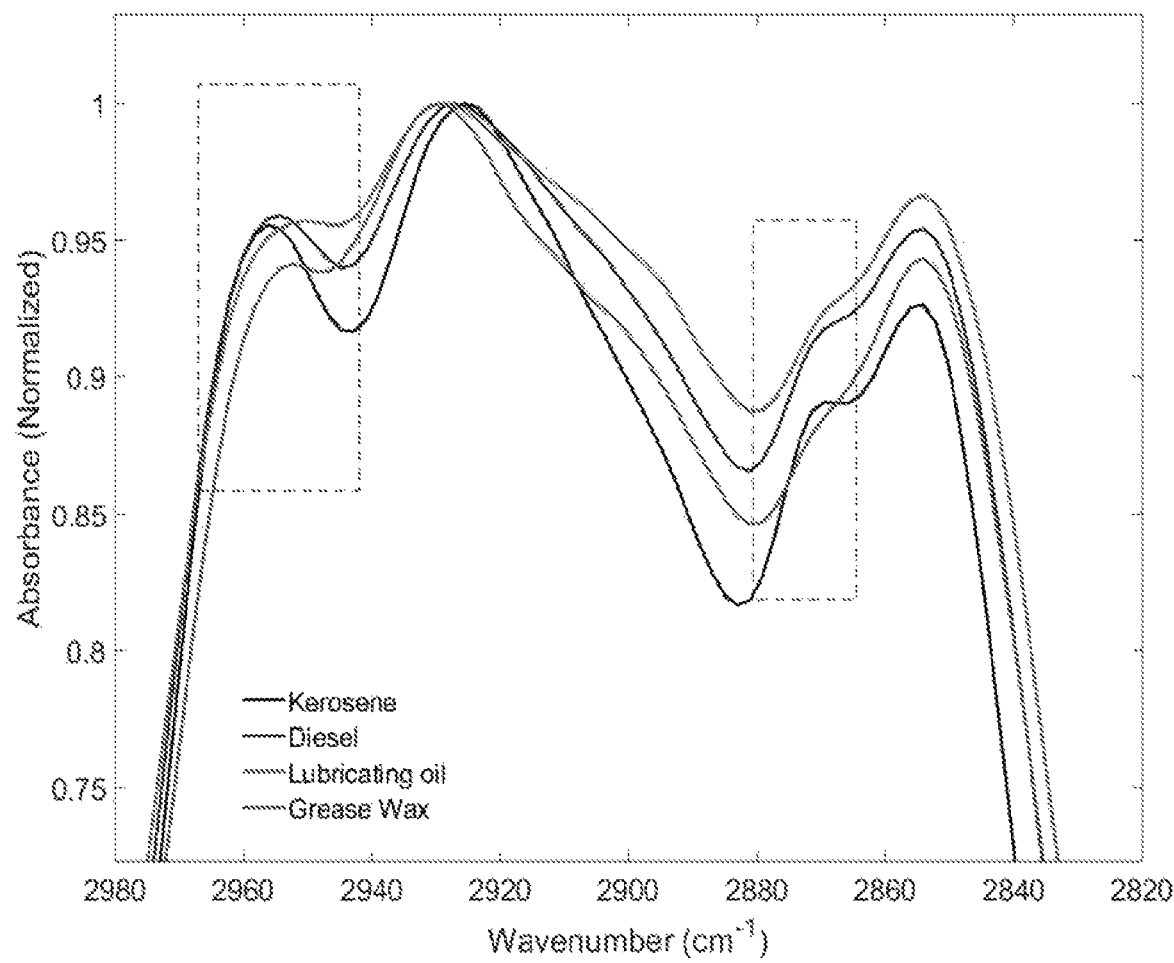
FIG. 8 shows the FTIR spectra data for the samples of FIGS. 6a-6d at wavenumbers between 3000 and 2800 $cm^{-1}$.

FIG. 8 demonstrated the bands of the four products in the region. As mentioned the band at 2950 cm$^{-1}$ increases adversely with the $C_n$ from $C_{20}$ to $C_{37}$. By comparison, it is clear to observe that a higher intensive band at 2950 cm$^{-1}$ existed in IR spectrum of diesel and kerosene, rather than in the lubricating oil and grease wax. The study has shown that it is possible to determine the alkanes with different $C_n$ using their most presented characteristic bands. The phenomena of the three regions, 2954 to 2872 cm$^{-1}$, 1480 to 1450 cm$^{-1}$ and 750 to 730 cm$^{-1}$ can be applied for $C_n$ identification. However, unlike applying pure alkane chemicals to a KBr background. When a petroleum product is applied to soil, the soil IR spectrum will submerge the characteristic bands below 2000 cm$^{-1}$, due to the quartz and other soil components. Hence, for a soil sample, the first IR region mentioned above should be applied majorly to the alkane studies. Also, using this method, it is possible to determine the dominant fraction of $C_n$ in soil. However, the method may not be able to determinate each alkane in heterogeneous mixtures, especially in a complex background, such as a neutral soil.

Referring back to FIG. 2, there is a shown a flow chart of a method 100 of determining petroleum hydrocarbon fractions ($C_n$) in a sample, the method 10 including the steps of inputting 102 the sample into a chamber, emitting infrared light from an optical light source into the chamber with the sample, and detecting at a detector a detected infrared light from the chamber; transforming 104 the detected infrared light to a Fourier Transform Infrared (FTIR) spectrum of the sample at a processor, wherein the FTIR spectrum has wavenumbers between 4000 and 400 $cm^{-1}$; processing 106 the FTIR spectrum to identify sub-bands each having at least one doublet of sub-band peaks at respective wavenumbers in a second derivative curve of the FTIR spectrum using a second derivation algorithm implemented by the processor; comparing 108 the at least one doublet of sub-band peaks to data indicative of known doublets of sub-band peaks at known wavenumbers for petroleum hydrocarbon fractions in the FTIR spectrum to classify the petroleum hydrocarbon fractions in the sample; and determining 110 a dominant petroleum hydrocarbon fraction of the petroleum hydrocarbon fractions in the sample based on a ratio of intensities of the sub-band peaks of the at least one doublet for each of the petroleum hydrocarbon fractions in the sample.

It will be appreciated by those persons skilled in the art that further aspects of the method 100 will be apparent from the above description of the apparatus 10 and the examples. Further, the person skilled in the art will also appreciate that at least part of the method could be embodied in program code that implemented by a processor of the apparatus 10. The program code could be supplied in a number of ways, for example on a memory.

Those skilled in the art will also appreciate that the invention described herein is susceptible to variations and modifications other than those specifically described. It is to be understood that the invention includes all such variations and modifications.

TABLE 1

Orthogonal experimental design table (Unit: ppm or mg/kg).

| OED | $C_{20}$ | $C_{26}$ | $C_{32}$ | $C_{37}$ | Total |
|---|---|---|---|---|---|
| 1 | 10,000 | 5,000 | 10,000 | 500 | 25,500 |
| 2 | 10,000 | 10,000 | 500 | 2,500 | 23,000 |
| 3 | 5,000 | 500 | 10,000 | 2,500 | 18,000 |
| 4 | 5,000 | 10,000 | 5,000 | 500 | 20,500 |
| 5 | 5,000 | 5,000 | 500 | 5,000 | 15,500 |
| 6 | 500 | 10,000 | 10,000 | 5,000 | 25,500 |
| 7 | 500 | 500 | 500 | 500 | 2,000 |
| 8 | 10,000 | 500 | 5,000 | 5,000 | 20,500 |
| 9 | 500 | 5,000 | 5,000 | 2,500 | 13,000 |

TABLE 2

Selected petroleum products

| Product type | Product Name | Carbon chains | Density |
|---|---|---|---|
| Kerosene | Diggers | $C_{10}$ to $C_{18}$ | 0.76 |
| Diesel | Caltex | $C_{19}$ to $EC_{30}$ | 0.81 |
| Lubricating Oil | Gear Oil, 85W-140, Penrite | $>EC_{30}$ | 0.90 |
| Grease Wax | Grease Valpex, Valvoline | $>EC_{30}$ | 0.97 |

The invention claimed is:

1. A method of determining petroleum hydrocarbon fractions ($C_n$) in a sample, the method including:
    inputting the sample into a chamber;
    emitting infrared light from an optical light source into the chamber with the sample;
    detecting at a detector a detected infrared light from the chamber;
    transforming the detected infrared light to a Fourier Transform Infrared (FTIR) spectrum of the sample at a processor, wherein the FTIR spectrum has wavenumbers between 4000 and 400 $cm^{-1}$;
    processing the FTIR spectrum to identify sub-bands each having at least one doublet of sub-band peaks at respective wavenumbers in a second derivative curve of the FTIR spectrum using a second derivation algorithm implemented by the processor;
    comparing the at least one doublet of sub-band peaks to data indicative of known doublets of sub-band peaks at known wavenumbers for petroleum hydrocarbon fractions in the FTIR spectrum to classify the petroleum hydrocarbon fractions in the sample; and
    determining a dominant petroleum hydrocarbon fraction of the petroleum hydrocarbon fractions in the sample based on a ratio of intensities of the sub-band peaks of the at least one doublet for each of the petroleum hydrocarbon fractions in the sample;
    wherein the at least one doublet includes a first doublet of sub-band peaks at wavenumbers between 3000 and 2800 $cm^{-1}$.

2. A method of claim 1, wherein the first doublet of sub-band peaks is at wavenumbers 2954 and 2827 $cm^{-1}$.

3. A method of claim 2, wherein the at least one doublet further includes a second doublet of sub-band peaks at wavenumbers between 1500 and 1400 $cm^{-1}$.

4. A method of claim 3, wherein the second doublet of sub-band peaks is at wavenumbers between 1480 and 1450 $cm^{-1}$.

5. A method of claim 3, wherein the at least one doublet of sub-band peaks further includes a third doublet of sub-band peaks at wavenumbers between 750 and 700 $cm^{-1}$.

6. A method of claim 5, wherein the third doublet of sub-band peaks is at wavenumbers between 750 and 730 $cm^{-1}$.

7. A method of claim 5, wherein the sample is soil and the second doublet and the third doublet of sub-band peaks are obscured in the FTIR spectrum by sub-bands for components of the soil.

8. A method of claim 1 further including performing baseline correction of the FTIR spectrum using a baseline correction algorithm implemented by the processor to: locate points on the FTIR spectrum representing wavenumbers with low absorbance values corresponding to valleys in the FTIR spectrum; recursively drawing a new baseline from both sides of the valleys to sides of the FTIR spectrum using straight lines; disregard ones of the points on the FTIR spectrum with absorbance values lower than the straight lines; and generate a baseline corrected FTIR spectrum by connecting remaining ones of the points on the FTIR spectrum.

9. A method of claim 8, further including processing the baseline corrected FTIR spectrum to identify the sub-bands.

10. A method of claim 9, further including filtering the baseline corrected FTIR spectrum using a Gaussian filter algorithm implemented by the processor to remove ones of the sub-bands having sub-band valleys higher than a threshold value in the second derivative curve, wherein the Gaussian filter algorithm is a Gaussian low pass filter algorithm with a standard deviation of 1.5.

11. A method of claim 1, further including optimising identification of the sub-bands in the second derivative curve using an optimisation algorithm implemented by the processor to minimise a difference between a smoothed second derivative curve and the second derivative curve having the identified sub-bands, wherein the optimisation algorithm is a Monte Carlo algorithm.

12. An apparatus for determining petroleum hydrocarbon fractions ($C_n$) in a sample, the apparatus including:
 a housing;
 a chamber disposed in the housing for inputting the sample therein;
 an optical light source disposed in the housing for emitting infrared light into the chamber with the sample;
 a detector for detecting a detected infrared light from the chamber; and
 a controller disposed in the housing having a processor and a memory in data communication with the processor, the controller being configured to:
 transform the detected infrared light to a Fourier Transform Infrared (FTIR) spectrum of the sample at a processor, wherein the FTIR spectrum has wavenumbers between 4000 and 400 $cm^{-1}$;
 process the FTIR spectrum to identify sub-bands each having at least one doublet of sub-band peaks at respective wavenumbers in a second derivative curve of the FTIR spectrum using a second derivation algorithm implemented by the processor;
 compare the at least one doublet of sub-band peaks to data indicative of known doublets of sub-band peaks at known wavenumbers for petroleum hydrocarbon fractions in the FTIR spectrum to classify the petroleum hydrocarbon fractions in the sample; and
 determine a dominant petroleum hydrocarbon fraction of the petroleum hydrocarbon fractions in the sample based on a ratio of intensities of the sub-band peaks of the at least one doublet for each of the petroleum hydrocarbon fractions in the sample;
 wherein the at least one doublet includes a first doublet of sub-band peaks at wavenumbers between 3000 and 2800 $cm^{-1}$.

13. An apparatus of claim 12, wherein the first doublet of sub-band peaks is at wavenumbers 2954 and 2827 $cm^{-1}$.

14. An apparatus of claim 13, wherein the at least one doublet further includes a second doublet of sub-band peaks at wavenumbers between 1500 and 1400 $cm^{-1}$.

15. An apparatus of claim 14, wherein the second doublet of sub-band peaks is at wavenumbers between 1480 and 1450 $cm^{-1}$.

16. An apparatus of claim 13, wherein the at least one doublet of sub-band peaks further includes a third doublet of sub-band peaks at wavenumbers between 750 and 700 $cm^{-1}$.

17. An apparatus of claim 16, wherein the third doublet of sub-band peaks is at wavenumbers between 750 and 730 $cm^{-1}$.

18. An apparatus of claim 16, wherein the sample is soil and the second doublet and the third doublet of sub-band peaks are obscured in the FTIR spectrum by sub-bands for components of the soil.

19. An apparatus of claim 18, wherein the apparatus is located near the sample.

* * * * *